US012618883B2

(12) United States Patent
Roberts

(10) Patent No.: US 12,618,883 B2
(45) Date of Patent: May 5, 2026

(54) METHODS FOR CALCULATING A RELATIVE CHANGE IN PERCENT VOIDS USING ELECTROMAGNETIC WAVE REFLECTION COEFFICIENTS

(71) Applicant: GEOPHYSICAL SURVEY SYSTEMS, INC., Nashua, NH (US)

(72) Inventor: Roger Roberts, Amesbury, MA (US)

(73) Assignee: GEOPHYSICAL SURVEY SYSTEMS, INC., Nashua, NH (US)

( * ) Notice: Subject to any disclaimer, the term of this patent is extended or adjusted under 35 U.S.C. 154(b) by 572 days.

(21) Appl. No.: 18/169,353

(22) Filed: Feb. 15, 2023

(65) Prior Publication Data

US 2023/0194588 A1      Jun. 22, 2023

Related U.S. Application Data

(63) Continuation-in-part of application No. 17/990,860, filed on Nov. 21, 2022, now Pat. No. 11,835,558, which is a continuation of application No. 17/209,338, filed on Mar. 23, 2021, now Pat. No. 11,513,146.

(Continued)

(51) Int. Cl.
*G01R 27/26* (2006.01)
*G01N 33/38* (2006.01)

(52) U.S. Cl.
CPC ....... *G01R 27/2617* (2013.01); *G01N 33/383* (2013.01)

(58) Field of Classification Search
CPC ............. G01R 27/2617; G01N 33/383; G01N 15/088; G01N 2203/0066; G01N 2203/0067; G01N 2015/0833
See application file for complete search history.

(56) References Cited

U.S. PATENT DOCUMENTS 5,952,561 A  * 9/1999 Jaselskis ................ G01N 33/42
73/78
2002/0162383 A1* 11/2002 Regimand ................ G01N 9/02
73/38

(Continued)

OTHER PUBLICATIONS

Hoegh, K., Roberts, R., Dai, S., & Teshale, E. Z. (2019). Toward Core-Free Pavement Compaction Evaluation: An Innovative Method Relating Asphalt Permittivity to Density. Geosciences, 9(7), 280. (Year: 2019).*

*Primary Examiner* — Catherine T. Rastovski
*Assistant Examiner* — Sharad Timilsina
(74) *Attorney, Agent, or Firm* — Michael J. Feigin, Esq.; Feigin and Fridman LLC

(57) ABSTRACT

A method for calculating the change in percent voids between a reference location and a second location in a medium. The method includes obtaining a reference reflection coefficient of an electromagnetic wave reflection at the reference location, and a second reflection coefficient of an electromagnetic wave reflection at the second location. The obtained reflection coefficients are used to calculate a percent change in reflection coefficient. A reflection conversion factor correlating the change in the reflection coefficient to a change in percent voids in the medium is calculated and is used to calculate a change in percent voids between the reference and second locations based on the calculated percent change in reflection coefficients.

5 Claims, 12 Drawing Sheets

Related U.S. Application Data

(60) Provisional application No. 63/140,292, filed on Jan. 22, 2021.

(56) References Cited

U.S. PATENT DOCUMENTS

| | | | | |
|---|---|---|---|---|
| 2005/0150278 A1* | 7/2005 | Troxler | .................. | G01N 33/42 |
| | | | | 73/78 |
| 2017/0199298 A1* | 7/2017 | Hu | .......................... | E21B 33/14 |

* cited by examiner

Figure 10

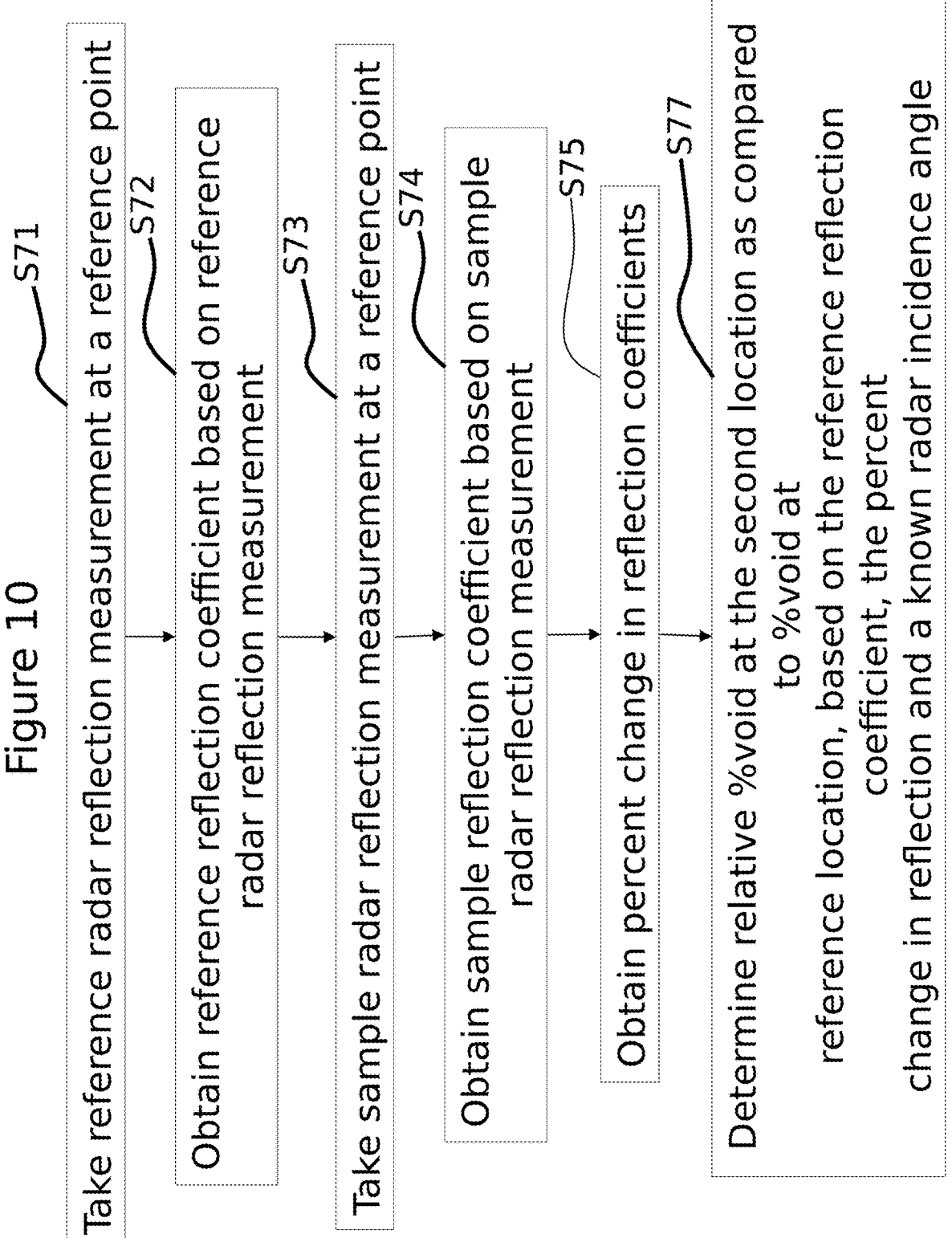

S71 — Take reference radar reflection measurement at a reference point

S72 — Obtain reference reflection coefficient based on reference radar reflection measurement S73 — Take sample radar reflection measurement at a reference point S74 — Obtain sample reflection coefficient based on sample radar reflection measurement S75 — Obtain percent change in reflection coefficients S77 — Determine relative %void at the second location as compared to %void at reference location, based on the reference reflection coefficient, the percent change in reflection and a known radar incidence angle

METHODS FOR CALCULATING A RELATIVE CHANGE IN PERCENT VOIDS USING ELECTROMAGNETIC WAVE REFLECTION COEFFICIENTS

FIELD OF THE DISCLOSED TECHNOLOGY

The disclosed technology relates generally to methods for computing a change in compaction of asphalt concrete, and, more specifically, to methods for calculating a relative change in compaction of asphalt concrete measured at two measurement locations.

BACKGROUND OF THE DISCLOSED TECHNOLOGY

There is a need easily and accurately to know the variation in density of a new asphalt road as it is being placed, since controlling its density can double the life of the road. Ground Penetrating Radar (GPR) technology is often used to measure the effective dielectric of asphalt of road surfaces. Knowledge of the effective dielectric of asphalt is useful in calculating the density of the asphalt. Once a calibration equation mapping dielectric to air void content is created, the density can be known simply by measuring the dielectric value at a given location on the road.

The prior art describes a method of generating the calibration equation mapping between air void content and dielectric, based only on a known percent compaction and associated dielectric of a single sample of asphalt. This calibration method, though efficient, requires the procurement of at least one sample of asphalt with associated measured dielectric and % voids. The step of obtaining a sample of material with these known values may, at times, be difficult or impossible, for example due to lack of access to, or availability of, the equipment necessary for obtaining the sample.

Even when calibration is unavailable, knowledge of the spatial variation in % voids can help reveal problems in the placement of asphalt. These problems can be corrected once known. For example, measuring the expected range in % voids between the center of a paved area and edges of the paved area can help identify problems in the placement of the asphalt. More generally, mapping of the relative change in compaction over a paved area enables adjusting of the roller compaction strategy accordingly, and assists in avoiding over-compaction or under-compaction. A stakeholder may also decide to reward or penalize the paving contractor based on the uniformity in % void content.

There is thus a need in the art for a method of calculating the relative change in air void content between two or more measurement locations, when the measurement is conducted in situ.

SUMMARY OF THE DISCLOSED TECHNOLOGY

The disclosed technology relates generally to methods for computing relative percent voids, and, more specifically, to methods for calculating a relative percent voids at two asphalt locations, in situ, using radar reflection amplitudes.

This disclosure should be interpreted according to the definitions below. In case of a contradiction between the definitions in this Definitions section and other sections of this disclosure, this section should prevail.

Dielectric—an electromagnetic property that relates to the ability of a material to store energy in the presence of an electric field.

Effective Dielectric—an average dielectric of a micro-inhomogeneous medium, i.e. a medium whose dielectric is not homogeneous on a small scale.

Asphalt—a composite material comprising and having at least 90% aggregate (i.e. rock fragments) and bitumen, and, in some cases, also including additional materials. Also known as "pavement" in North America and as "asphalt concrete" in technical papers. These terms are used interchangeably.

Dielectric Mixing Equation—an equation that calculates the effective dielectric of a dielectrically inhomogeneous medium, given volume percentages and dielectrics of constituents in the medium.

Asphalt Air Void Content—the percentage or volume ratio of air in an asphalt sample.

Bitumen—a black viscous mixture of hydrocarbons obtained naturally or as a residue from petroleum distillation. Bitumen is commonly used as a constituent in asphalt concrete. It may also be called tar or binder.

Aggregate—rock and sand constituents typically included in asphalt concrete. Aggregates may be taken from nearby quarries, and as such, have highly regional material properties (shape, density, dielectric, porosity etc.).

Air Void—air trapped inside asphalt concrete. The total air void content is typically expressed as a percentage of the total volume of asphalt concrete.

Puck—a cylindrical-shaped asphalt sample that is typically compacted to a pre-determined amount using gyratory compactor.

Percent Compaction—the inverse of the percent voids in a sample, or the percent of the sample which is not air voids. A sample of asphalt that has one hundred percent compaction contains no air voids. Percent compaction is calculated from % Voids using the relation: % Compaction=100–% Voids.

Magnetic Permeability—an electromagnetic property that relates the magnetic induction inside a material to the magnetic field intensity.

Mix Design—a particular combination of aggregate, bitumen and possibly other constituents that are mixed together to make asphalt. Different mix designs are customized for the locations where the asphalt is to be used.

Gmm—the ideal specific gravity of an asphalt mix with 0% air voids.

Gmm Dielectric—the ideal dielectric of an asphalt mix with 0% air voids.

Percent Gmm—another term for the percentage of asphalt compaction. Percent Gmm is calculated from % voids using the relation: % Gmm=100–% Voids.

In accordance with an embodiment of the disclosed technology, there is provided a method for calculating a relative percent voids in an asphalt region using two Radar reflection measurements obtained at two different locations in the asphalt region.

A relationship between the change in reflection amplitude and the change in % voids is derived from two equations: (1) an equation used to calculate of the effective dielectric of an asphalt mix versus air void content; and (2) the Fresnel equation describing the reflection characteristics of an electromagnetic wave at the boundary between two media with different electromagnetic properties.

In some embodiments of the disclosed technology, the effective dielectric of an asphalt mix at various percent void contents is calculated based on the M-HS equation:

$$\epsilon = \left( \epsilon_e + \cfrac{f}{\cfrac{1}{\epsilon_i - \epsilon_e} + \cfrac{1-f}{3\epsilon_e}} + \epsilon_i + \cfrac{1-f}{\cfrac{1}{\epsilon_e - \epsilon_i} + \cfrac{f}{3\epsilon_i}} \right) \Big/ 2$$

where:

$\epsilon$ is the dielectric measurement of the single asphalt sample;

$\epsilon_e$ is the Gmm dielectric of the asphalt mix;

$\epsilon_i$ is the dielectric of air; and f is a volume fraction of air in the single puck.

In some embodiments, the effective dielectric of an asphalt mix at various percent void content is calculated based on the Sen-Scala-Cohen equation.

$$\frac{\epsilon - \epsilon_i}{\epsilon_i - \epsilon_e} = f\left(\frac{\epsilon}{\epsilon_i}\right)^{\frac{1}{3}}$$

In some embodiments, the method includes calculating a change in % voids based on a known relationship between changes in % voids associated changes in the reflection coefficient for a range of expected Gmm dielectrics, for example, utilizing equations used to calculate the effective dielectric and the reflection coefficient. The calculated change in % voids vs. % change in reflection coefficient may be plotted graphically, where, for each Gmm dielectric, the resulting plot is substantially linear. The slope of the plot is termed the % voids–percent reflection coefficient (PV-PRC) slope. As a consequence, the % change in voids is calculated from the percent change in reflection coefficient using the following equation:

$$\% \ \Delta PV \approx \% \ \Delta\rho(PV\text{-}PRC)$$

Where % $\Delta PV$=change in percent voids;

% $\Delta\rho$=percent change in reflection coefficient;

PV-PRC=slope of line relating change in % voids to % change in reflection coefficient.

It is observed from the preceding equation that all that is needed to calculate the change in percent voids between two reflection coefficient measurements is the PV-PRC slope. Of particular interest is the error introduced by various methods of calculating the PV-PRC slope. Variation in PV-PRC slopes over the approximate range of typical Gmm dielectrics for a common incidence angle is approximately 0.066. A maximum uncertainty in calculated % voids over a range of ±10% voids may be calculated using the average PV-PRC slope to be 0.033*10=±0.33% voids.

The change in % voids over a range of ±10% voids may be calculated more accurately, with uncertainty reduced to a more desirable ±0.20% voids by using a PV-PRC slope that more closely matches the expected Gmm Dielectric for the mix, rather than the average PV-PRC slope. This may be accomplished by calculating the PV-PRC slope that corresponds to an assumed 10% void content, associated with the first dielectric measurement, and using that calculated PV-PRC slope to compute the change in % voids between the first and second measurements.

The change in % voids over a range of ±10% voids may be computed even more accurately, with uncertainty further reduced, by choosing a PV-PRC slope that matches the pre-determined, or previously known, approximate Gmm dielectric for the mix.

In some embodiments, the change in % voids can be related to the change in calculated dielectrics between two reflection measurements. The variation in slopes of the lines formed by plots of the calculations described above for different Gmm dielectrics, however, shows greater than 1.0% void calculation uncertainties. More accurate results are obtained by converting the dielectrics to representative reflection coefficients and using an appropriate dielectric mixing equation and Fresnel's equations.

It is understood that the use of % voids can be interchanged with percent Gmm and percent compaction in all the calculations by simply subtracting the % voids value from 100. Thus, the scope of the invention also applies to applications where the desired output is percent compaction or percent Gmm.

In accordance with an embodiment of the disclosed technology, there is provided a method for determining a change in percent voids between a reference location and a second location in a medium. The method includes obtaining a reference reflection coefficient of an electromagnetic wave reflection at the reference location, and obtaining a second reflection coefficient of the electromagnetic wave reflection at the second location. The method further includes obtaining a percent change of reflection coefficients between the reference reflection coefficient and the second reflection coefficient, and obtaining a reflection conversion factor correlating changes in reflection coefficient to changes in percent voids in the medium. The method additionally includes, using the reflection conversion factor, generating the change in percent voids between the reference location and the second location based on the determined percent change of reflection coefficients.

In some embodiments, obtaining the reference reflection coefficient comprises obtaining multiple radar measurements over an area, using a radar system, and determining the reference reflection coefficient is based on an average of reflection coefficients for the multiple radar measurements.

In some embodiments, the method further includes repeating steps (b) to (e) for multiple sample locations in an area of the medium, each sample location comprising a the second location, and generating a spatial distribution map of the area of the medium, the spatial distribution map indicating the change in percent voids at the multiple sample locations in the area of the medium.

In some embodiments, obtaining the reference reflection coefficient comprises determining a dielectric of the medium based on a known Gmm dielectric of the medium and a specified percent voids.

In some embodiments, obtaining the reference reflection coefficient comprises obtaining a reference radar reflection measurement at the reference location, using a radar system, and using the reference radar reflection measurement to determine the reference reflection coefficient.

In some embodiments, obtaining the second reflection coefficient comprises obtaining a second radar reflection measurement at the second location, using the radar system, and using the second radar reflection measurement to determine the second reflection coefficient.

In some embodiments, obtaining the reference reflection and second reflection coefficients comprise obtaining a ratio of respective reflection amplitudes from an asphalt surface to a reflection amplitude from a more highly conducting surface. In some such embodiments, obtaining a percent change in reflection coefficients from the reference reflection coefficient and the second reflection coefficient comprises calculating the percent change in surface reflection amplitudes between measurements at the reference and second locations.

In some embodiments, obtaining the reference reflection coefficient and obtaining the second reflection coefficient comprise obtaining dielectric values at the reference location and at the second location by a system which is devoid of a radar antenna, and determining the reference reflection coefficient and the second reflection coefficient based on the corresponding dielectric values.

The various embodiments of the disclosed technology relate changes in measured or calculated to electromagnetic reflection coefficients to changes in % voids. Specifically, the change in % voids is approximately linearly related to the % change in reflection coefficient. The slope of the line in a plot of % voids versus % change in reflection coefficient, denoted as the PV-PRC slope, is approximately known to a sufficient degree of confidence for the range of asphalt mixes and % voids of interest to the practitioner. Therefore, the change in % voids between two reflection coefficient measurements is directly calculatable. And, importantly, no knowledge of the dielectric properties of the asphalt mix is necessary for this calculation. The envisioned typical use of the invention would entail making a reflection coefficient measurement at one location to serve as a reference and calculating the change in percent voids at other locations relative to the reference location from reflection coefficient measurements at these other locations. It is recognized that the percent change in reflection coefficients can be calculated directly from the surface reflection amplitudes at the two locations without the need to convert the measurements to reflection coefficients. Another envisioned use would be to obtain a measurement of a certain value, such as a dielectric, at a reference location and converting this value to its equivalent reflection coefficient using, for example, Fresnel's equations. A second measurement at a separate location is similarly converted to its equivalent reflection coefficient and then these two reflection coefficients are used to calculate the change in % voids between the two locations. Therefore, any two measurements that can be converted to reflection coefficients can be subsequently converted into a change in % voids.

BRIEF DESCRIPTION OF THE DRAWINGS

FIG. 10 is a block diagram of a method of obtaining a relative percent voids value from two different radar reflection measurements according to embodiments of the disclosed technology.

DETAILED DESCRIPTION OF EMBODIMENTS OF THE DISCLOSED TECHNOLOGY

The disclosed technology relates to methods for determining a change in % voids between measurements taken at two different locations using relative radar reflection coefficients.

Embodiments of the disclosed technology will become clearer in view of the following description and in view of the drawings.

In some embodiments, methods in accordance with the disclosed technology combine the M-HS equation and Fresnel's equation.

The M-HS equation is used to determine the effective dielectric of a medium with a known dielectric and known % air voids. The M-HS equation is given by equation 1:

$$\varepsilon_{eff} = \frac{\varepsilon_{Gmm} + \cfrac{\frac{PV}{100}}{\frac{1}{1-\varepsilon_{Gmm}} + \cfrac{1-\frac{PV}{100}}{3\varepsilon_{Gmm}}} + 1 + \cfrac{1-\frac{PV}{100}}{\frac{1}{\varepsilon_{Gmm-1}} + \cfrac{\frac{PV}{100}}{3}}}{2} \qquad \text{EQUATION 1}$$

Fresnel's equation is used to determine the reflection coefficient of an electromagnetic wave at the interface between two media possessing different electromagnetic properties.

Figure 1:
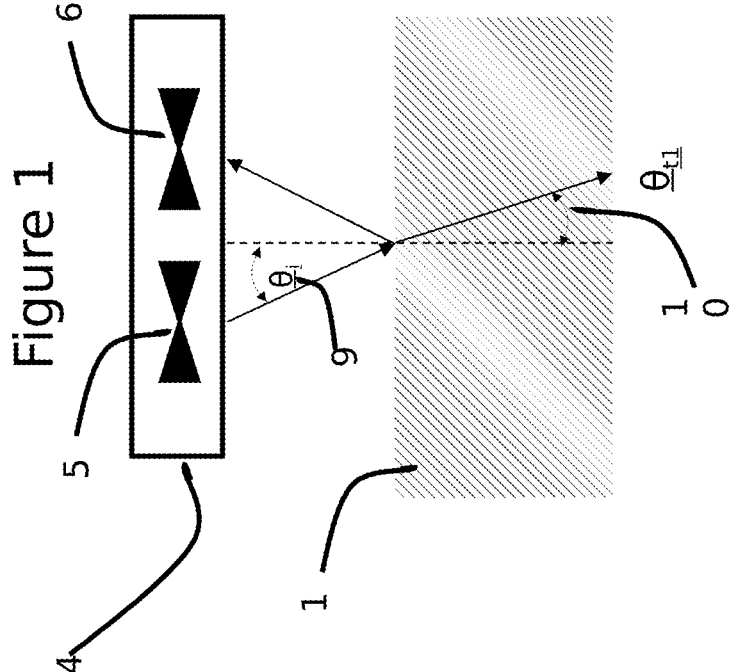
FIG. 1 is a schematic illustration of a system including transmitting and receiving radar antennas used to calculate a reflection coefficient from a sample of material, according to embodiments of the disclosed technology.

Turning to FIG. 1, it is seen that a given medium 1 has a known Gmm dielectric and a certain % voids (PV). An effective dielectric $\varepsilon_{eff}$ of the medium is determined using equation 1, where $\varepsilon Gmm$ is the Gmm dielectric of the medium, and PV is the percent void of the medium. In some embodiments, in which the effective dielectric and the Gmm dielectric of the medium are known, the equation can be rearranged to solve for % voids.

A radar system 4 includes transmitting and receiving antennas 5 and 6. System 4 is placed in a location exposed to air, at a predetermined distance from the medium 1. The dielectric of air, $\in_o$, is known in the art to be 1.0. Radar system 4 generates radar measurements, which can be used to compute a reflection coefficient, $\rho$. Keeping an incidence angle 9, $\theta_i$, at which the radar impinges upon the medium 1, fixed, the transmission angle, $\theta_t$ 10, at which the radar is transmitted through the medium, is a function of the effective dielectric of the medium. Specifically, the transmission angle $\theta_t$ can be computed by equation 2:

$$\theta_t = \sin^{-1}\left(\frac{\sin\theta_i}{\sqrt{\varepsilon_{eff}}}\right)$$

EQUATION 2

Given the effective dielectric of the medium, and the incidence and transmission angles of the radar, the reflection coefficient $\rho$ is given by equation 3:

$$\rho = \frac{\cos\theta_i - \sqrt{\varepsilon_{eff}}\,\cos\theta_t}{\cos\theta_i + \sqrt{\varepsilon_{eff}}\,\cos\theta_t}$$

EQUATION 3

The reflection coefficient equation or the transmission angle equation can be rearranged to solve for the effective dielectric, if the reflection coefficient and the incidence angle are known.

Figure 2:
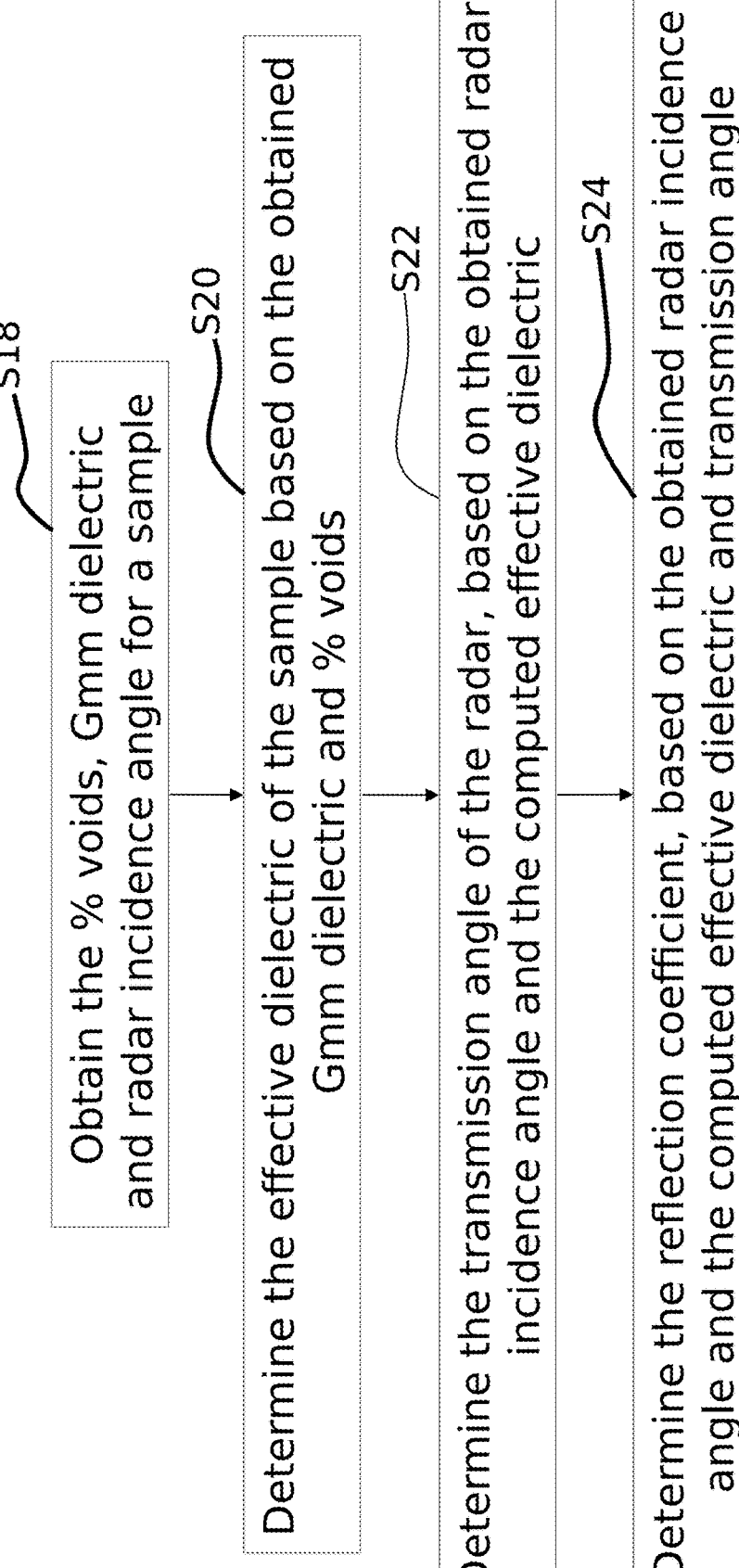
FIG. 2 is a schematic illustration of steps of a method used for calculating a reflection coefficient of a material with known Gmm dielectric and percent air voids and a known radar incidence angle.

The relationship between reflection coefficient variability and variability in % voids for an asphalt mix with a non-varying Gmm dielectric is determined in embodiments of the disclosed technology. This relationship will become apparent in the following exposition. FIG. 2 is a schematic illustration of steps of a method used for obtaining a reflection coefficient $\rho$ of a material. As seen, at step S18, % voids, Gmm dielectric, and radar incidence angle for the sample are obtained. At a step S20, equation 1 hereinabove is used to determine the effective dielectric of the sample from the input Gmm dielectric and % voids. At step S22, the effective dielectric determined in step S20, and the input radar incidence angle are used to obtain the transmission angle, based on equation 2. The effective dielectric determined in step S20, and the transmission angle determined at step S22, together with the known radar incidence angle, are used in step S24 to compute the corresponding reflection coefficient $\rho$ using equation 3 discussed hereinabove (Fresnel reflection coefficient equation).

Figure 3:
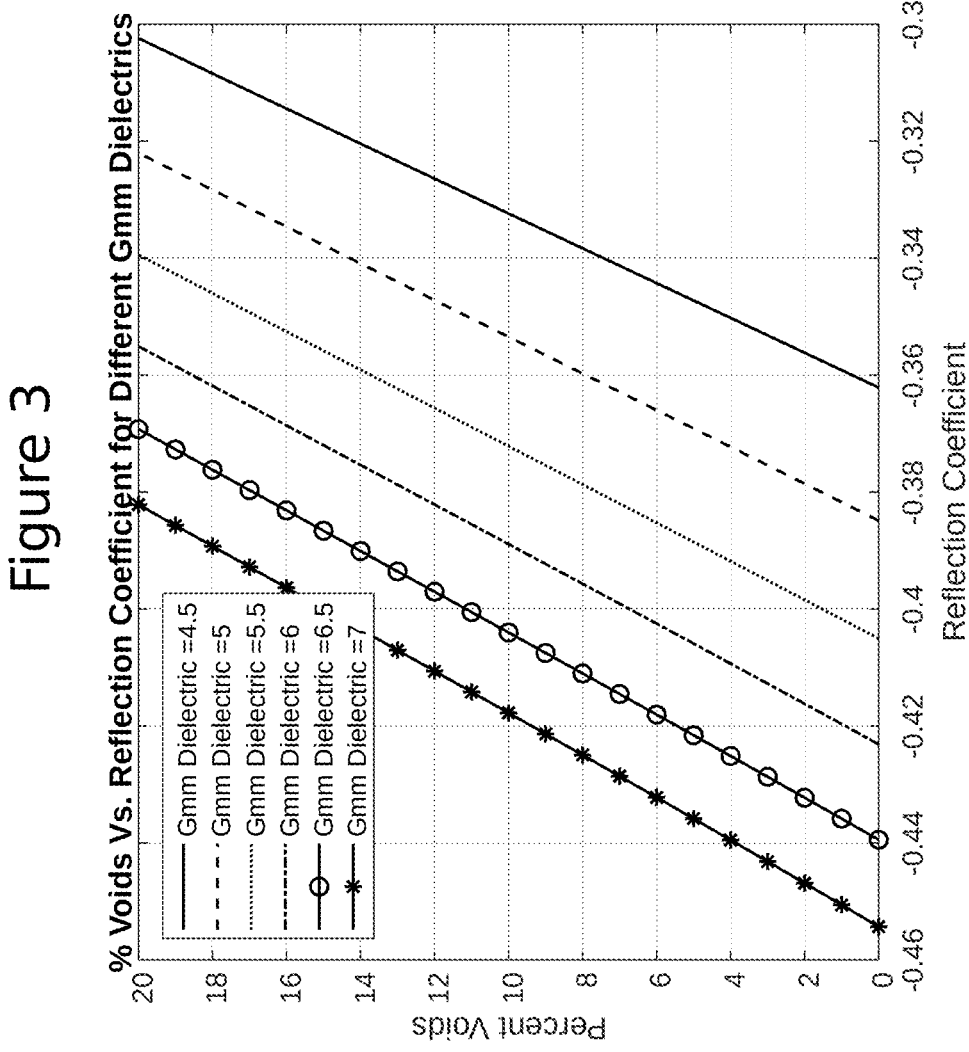
FIG. 3 are graphs of % voids versus reflection coefficient for different Gmm dielectrics.

One could use the method of FIG. 2, using multiple percent void values, a specific Gmm, and a specific radar incidence angle, to compute a range of corresponding reflection coefficients. FIG. 3 includes graphs of the reflection coefficient vs. the percent voids, for different Gmm dielectrics, based on a fixed radar incidence angle typically associated with measurements over compacted asphalt. As seen in FIG. 3, each line is substantially linear and the slopes of the lines are similar (i.e. the lines are substantially parallel to one another).

Figure 4:
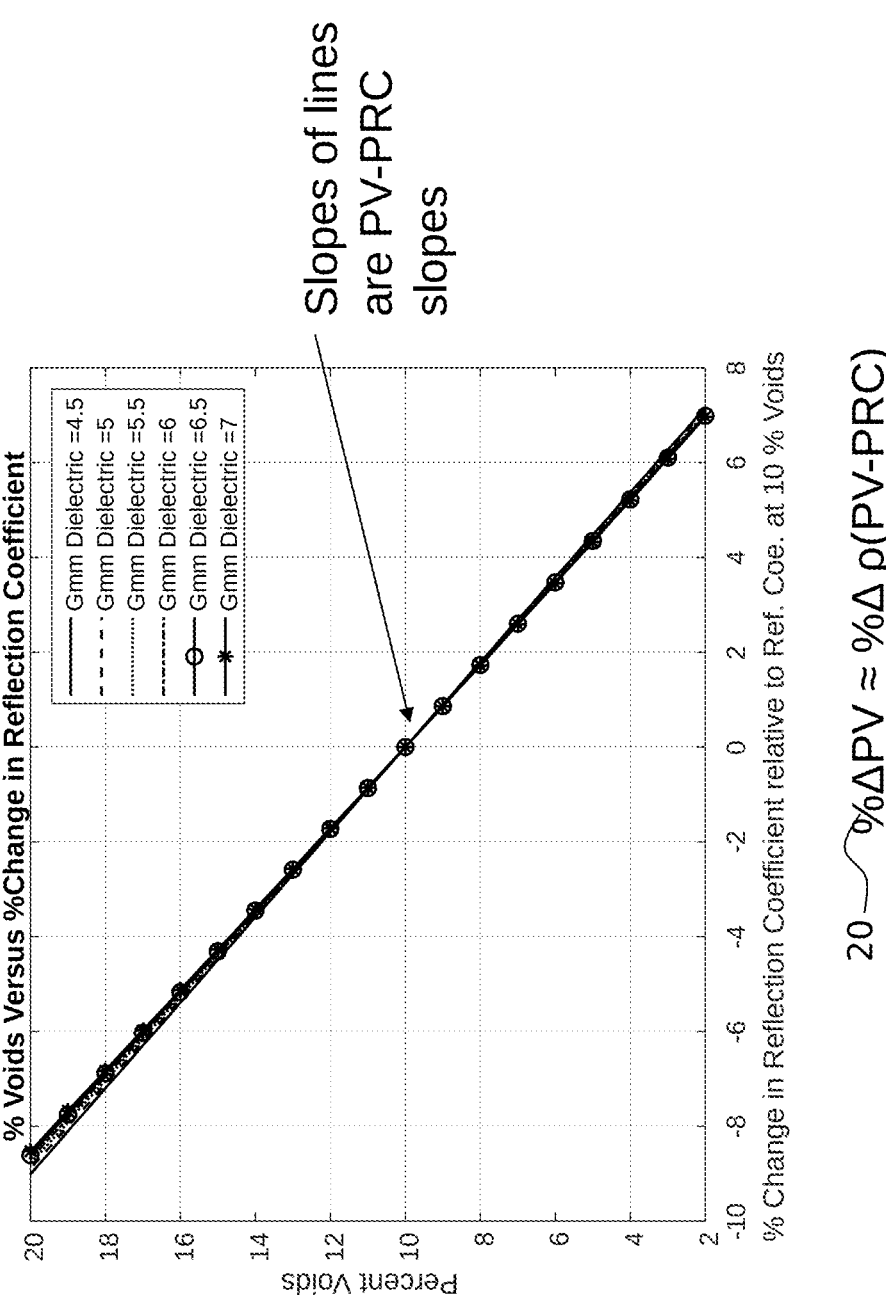
FIG. 4 are graphs of change in percent voids versus % change in reflection coefficient relative to the reflection coefficient at 10% voids, for materials possessing different Gmm dielectrics.

Another way to observe the similarity in the slopes of data generated using the method of FIG. 2, is to plot the % voids versus the percent change in reflection coefficient relative to a reflection coefficient corresponding to 10% voids. Results of such determinations are shown in FIG. 4, which illustrates that the graphs are nearly identical, having very similar PV-PRC slopes. From FIG. 4 it is evident that choosing a slope, the change in percent voids between two measurements can be approximately known just by multiplying the change in percent change in reflection coefficients to one of the PV-PRC slopes 20.

Figure 5:
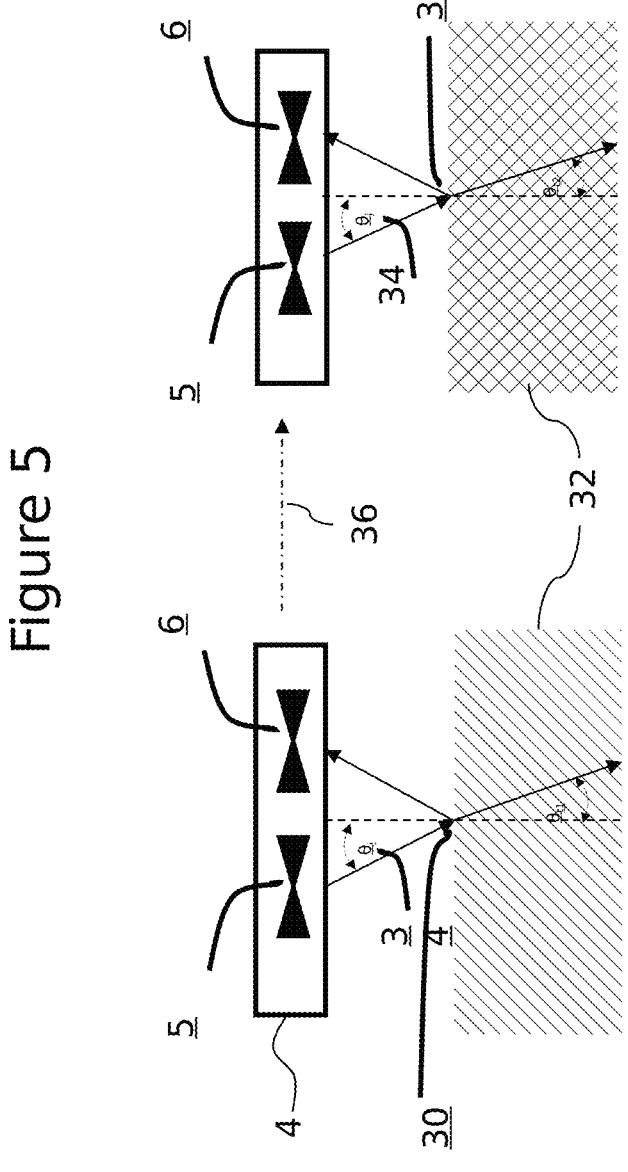
FIG. 5 is a schematic diagram of a dielectric measurement at two locations in an asphalt area according to embodiments of the disclosed technology.

The similarity of the PV-PRC slopes for different Gmm dielectric values has important implications, which are discussed with respect to FIG. 5. As seen in FIG. 5, the radar system 4 of FIG. 1 is used to obtain a first reflection coefficient measurement at a first location 30 of a medium 32, at a radar incidence angle 34. The radar system 4 is then moved along medium 32, in the direction of arrow 36, to a second location 38, and obtains a second reflection coefficient measurement at the second location, using the same radar incidence angle 34. It is assumed that the Gmm dielectric of Medium 32 is unknown, but the % voids at different locations of medium 32 may vary, as shown by the density of dot distribution in the two locations shown in FIG. 5.

A percent change in the reflection coefficient between first location 30 and second location 38 is obtained using equation 4:

% Δρ=100*(ρ2−ρ1)/ρ1      EQUATION 4%

A percent change in in the percent voids at second location 38 relative to first location 30 is calculated using the PV-PRC slope for each of values ρ1 (at location 30) and ρ2 (at location 38), as discussed above with respect to FIG. 4. Importantly, no knowledge of the Gmm dielectric is necessary and/or it is understood by a person carrying out embodiments of the disclosed technology that the Gmm dielectric remains constant, without an acceptable tolerance level.

Figure 6:
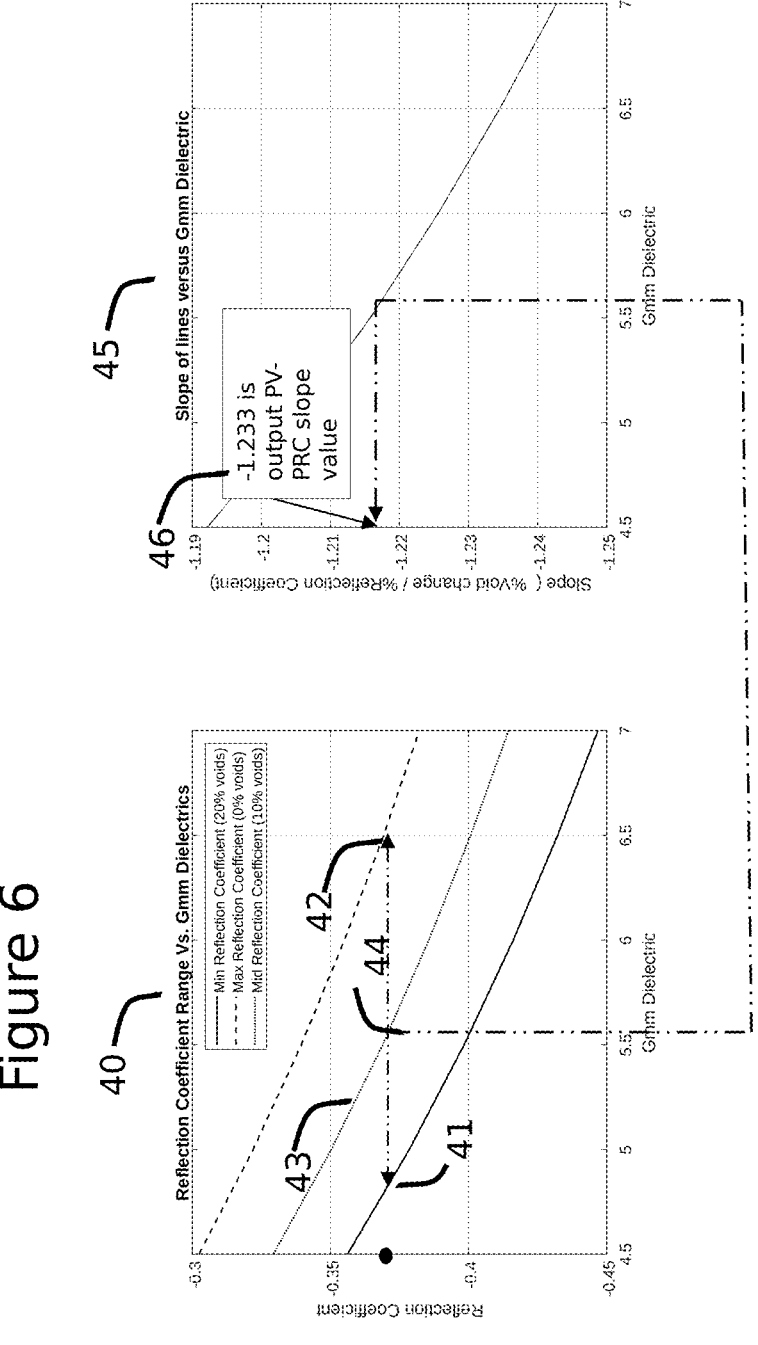
FIG. 6 graphically illustrates a method for obtaining a PV-PRC slope using a reflection coefficient obtained from a measurement.

FIG. 6 graphically illustrates a method for obtaining a PV-PRC slope using a reflection coefficient with a value of −0.37 obtained from a measurement. A first plot 40 illustrates a minimum plot of the reflection coefficients 41 corresponding to 20% voids in asphalt pavements possessing Gmm dielectrics ranging from 4.5 to 7. Similarly, a maximum plot of the reflection coefficients 42 corresponding to 0% void in asphalt pavements over the same range of Gmm dielectrics is shown. The midpoint plot of the reflection coefficients 43 corresponding to 10% voids is plotted midway between the 0 and 20% voids lines. As seen, the point on the midpoint plot 43 at a reflection coefficient of −0.37 corresponds to a Gmm Dielectric of about 5.57, indicated at reference numeral 44. The Gmm dielectric value is then used to extract from a plot 45 of the determined PV-PRC slopes versus Gmm dielectric to obtain a specific PV-PRC slope 46 value to be used in the relative % voids described hereinabove with respect to FIG. 5.

Figure 7:
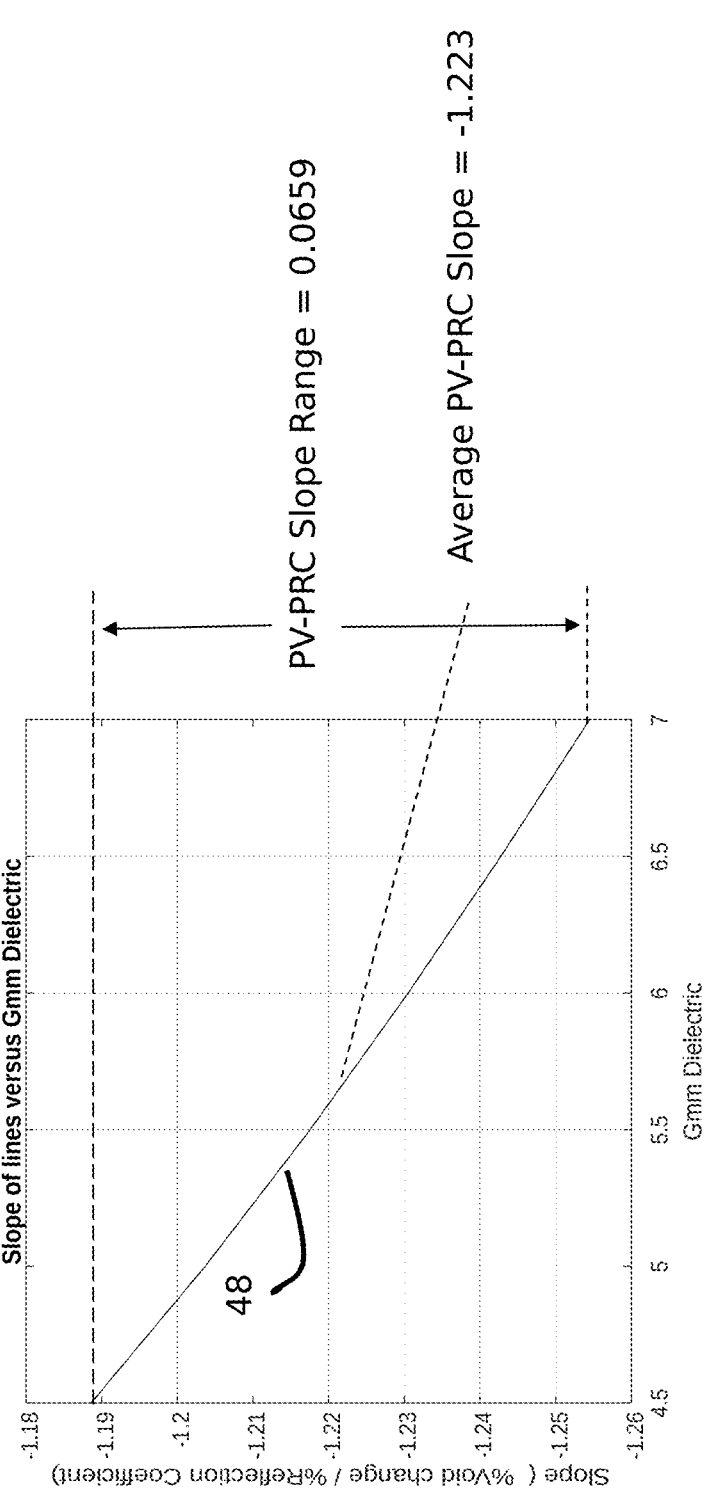
FIG. 7 is a graph of maximum error in PV-PRC slope when using an average PV-PRC slope value.

A maximum error in the PV-PRC slope can be determined for an expected range of Gmm dielectrics and corresponding % voids associated with asphalt pavements. A plot of the range of PV-PRC slope values versus Gmm dielectric at a typical fixed radar incidence angle is shown in FIG. 7. In the exemplary graph 48, the variation in the slope, over the typical range of Gmm dielectrics associated with asphalt, is −1.223±0.033. Consequently, the maximum error in relative percent voids using the average PV-PRC slope would be the 0.033 multiplied by the maximum difference in % voids, which is 20%. Thus, the maximum error is 0.033*20, which is 0.66%.

Figure 8:
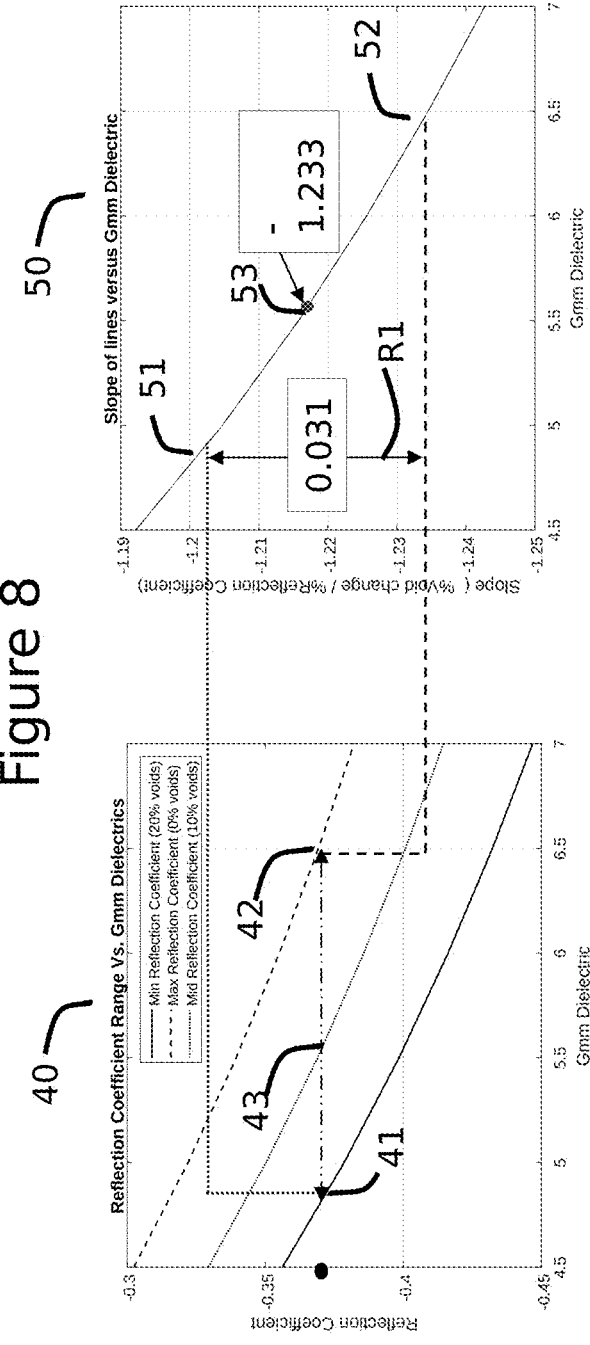
FIG. 8 graphically illustrates a method for obtaining a potential error in PV-PRC slope using a reflection coefficient corresponding to 10% voids according to embodiments of the disclosed technology.

Reference is now made to FIG. 8, which graphically illustrates a method for obtaining a potential error in PV-PRC slope using a reflection coefficient corresponding to 10% voids according to embodiments of the disclosed technology. Specifically, plot 40 (shown also in FIG. 6) is used to obtain the Gmm dielectric corresponding to 10% voids, for the corresponding reflection coefficient at point 43. The obtained value is used to compute the PV-PRC slope, at point 53 in a plot 50. Similarly, the PV-PRC slope is computed for 0% voids at point 52 on plot 50, and for 20% void at point 51 on plot 50. A maximum potential error in PV-PRC slope is approximately equal to one-half the range of PV-PRC slope values 51 and 52, the range indicated by R1. For the example illustrated in FIG. 8 the maximum error in relative percent voids is 0.031/2~0.016, and given that this is at 10% void, with the range of ±10% voids the maximum error associated with the PV-PRC slope is 0.16% voids.

Figure 9:
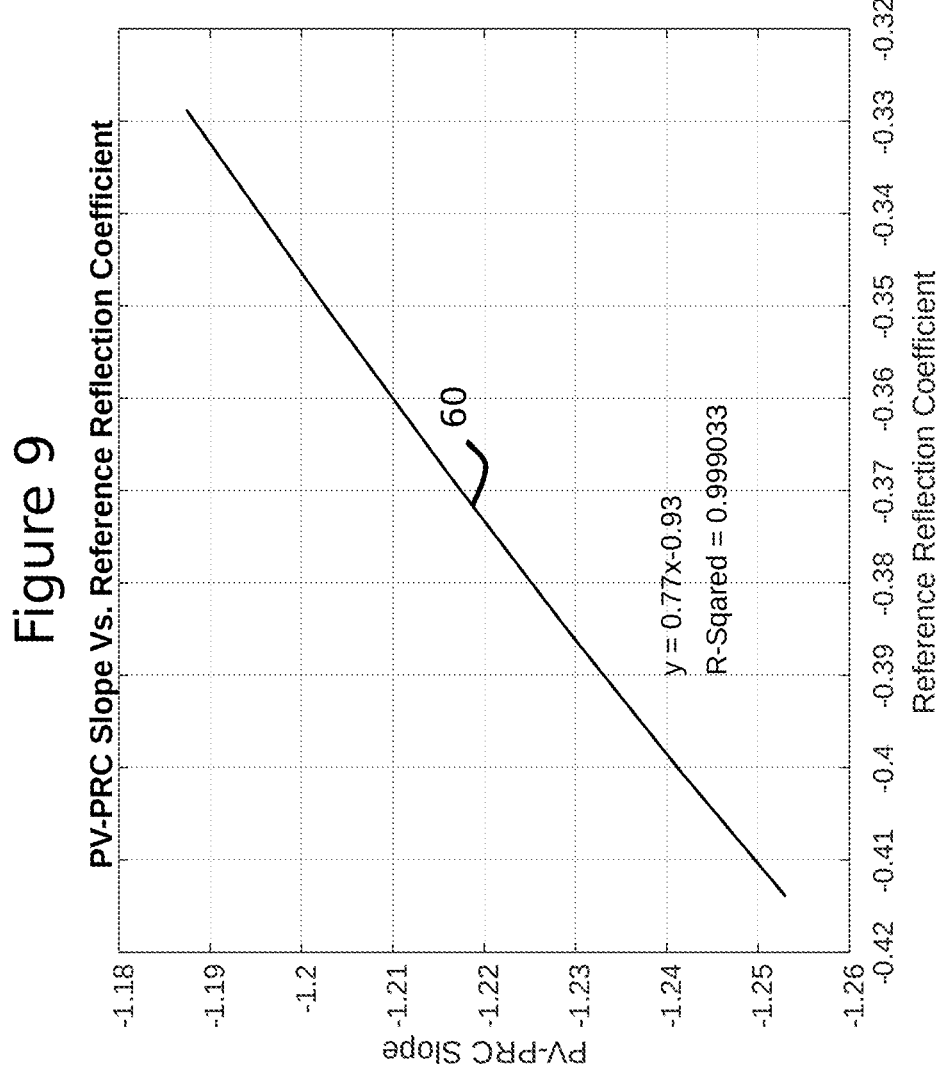
FIG. 9 is a graph of the derivation of a linear equation incorporating the PV-PRC slope.

FIG. 9 is a graph of the derivation of a linear equation incorporating the PV-PRC slope. In an embodiment of the disclosed technology, as shown, the PV-PRC slope corresponding to the mid-point % Voids 43 (shown in FIGS. 6 and 8) is determined based on the reflection coefficient to directly provide the PV-PRC for a given reference reflection coefficient. Furthermore, this relationship can be approximated by a linear equation 60 so as to reduce the relative % voids obtained as described hereinabove with respect to FIG. 5 to a linear equation, having with pre-set constants for a fixed incidence angle.

Specifically, if the linear equation is y=ax+b, the computation is given by equation 5:

$$\% \ \Delta PV \approx \% \ \Delta \rho (a\rho 1 + b) \qquad \text{EQUATION 5\%}$$

Where % ΔPV is the % void at a second location, relative to the % void at reference location;

% Δ ρ is the % change in the reflection coefficients between the reference location and the second location; and ρ1 is the reflection coefficient at the reference location.

Reference is now made to FIG. 10, which is a flow chart of a method for determining a relative percent void value from two different radar reflection measurements taken at two locations on a medium. At step S71, a reference radar reflection measurement is taken at a reference location, and a reference reflection coefficient is computed based on the obtained reference radar reflection measurement at step S72. Similarly, at step S73, a sample radar reflection measurement is taken at a second, sample location, and a sample reflection coefficient is computed based on the obtained reference radar reflection measurement at step S74. The percent change in reflection coefficients is determined in step S75, for example using equation 4 hereinabove. Finally, the reference reflection coefficient computed at step S72, together with the percent change in reflection coefficients computed at step S75 and with a known incidence angle, are used, at step S77, to compute the relative % voids at the second location as compared to the % void in the reference location.

The method of FIG. 10 may be repeated for multiple sample locations in a medium, such as an asphalt road. In such embodiments, the method may further include generating a distribution map of relative % void within the medium, which distribution map reflects the computed relative % void at each sample location.

Figure 11:
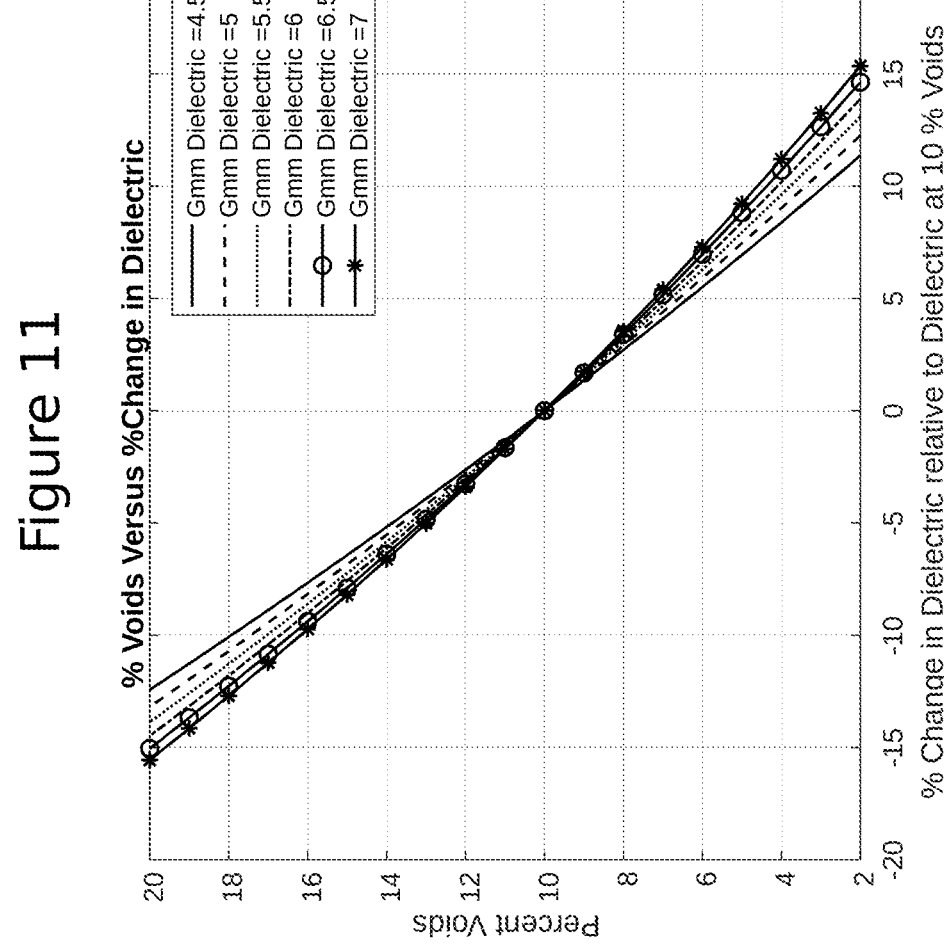
FIG. 11 is a graph of the relationship between % voids and % change in dielectric obtained from radar measurements of asphalt mixes possessing a range of typical Gmm dielectrics.

Reference is now made to FIG. 11 which is a graph of the relationship between % voids and % change in dielectric determined from radar measurements of asphalt mixes possessing a range of typical Gmm dielectrics. Specifically, FIG. 11 illustrates a plot of % voids versus the percent change in dielectric relative to the dielectric at 10% voids. The plot includes curves for different Gmm dielectrics. As seen, the percent change in dielectric is related, in a non-linear manner, to the % voids and is substantially dependent on the Gmm dielectric. Thus, the Inventors have recognized that the change in % voids directly from dielectric measurements at two locations generally cannot be determined sufficiently accurately. However, the inventors have identified that reflection coefficients associated with each dielectric can be determined for a specified incidence angle using Equation 3. Consequently and surprisingly, the inventors found that the change in percent voids between any two dielectric measurements may be determined by conversion of the dielectric values to reflection coefficients. As such, the dielectric measurement methodology is not limited to the scenario shown in FIG. 5. The method of computation of the disclosed technology may utilize a dielectric measurement obtained in any other mechanism or using any other methodology. For example, capacitive devices can be employed to measure the dielectric of the asphalt at two locations. Then, the dielectric values can be converted to reflection coefficients and subsequently the change in % voids of the asphalt between the two locations can be obtained in accordance with the disclosed technology.

Figure 12:
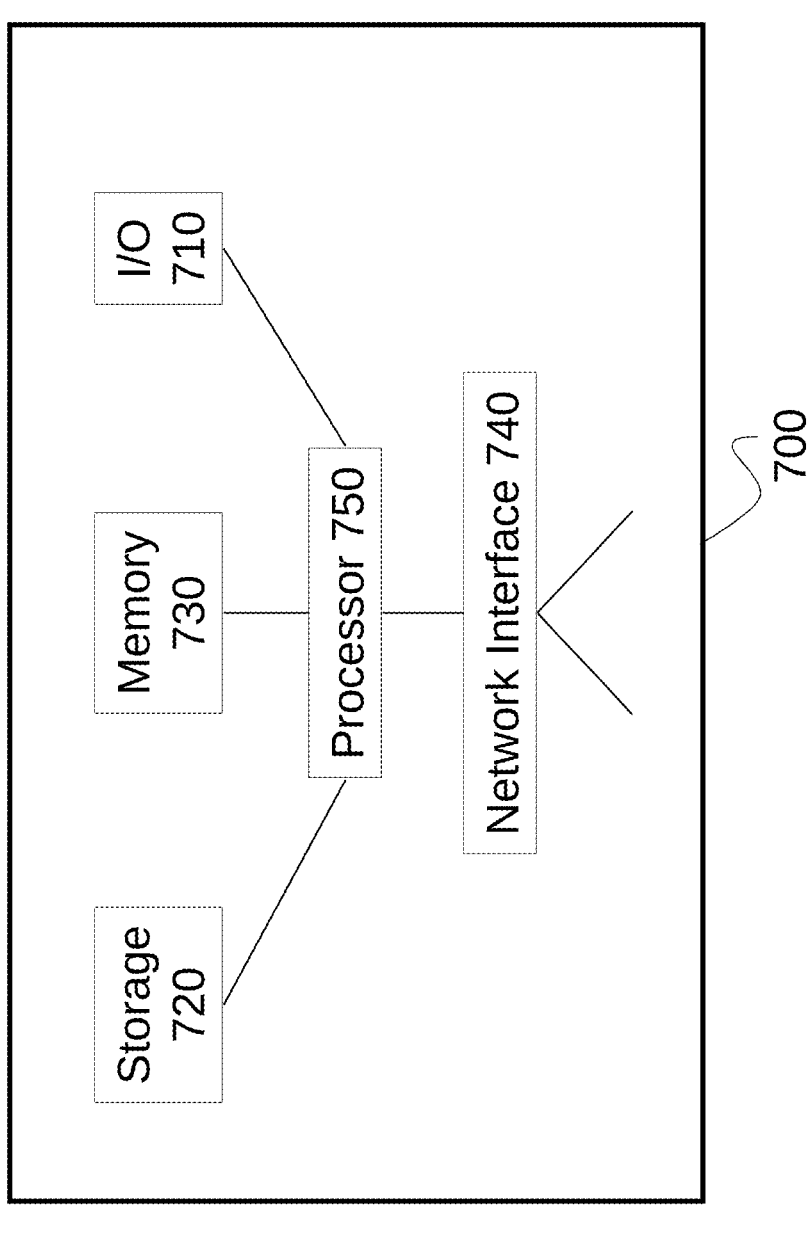
FIG. 12 shows a high-level block diagram of a device that may be used to carry out the disclosed technology.

FIG. 12 shows a high-level block diagram of a device that may be used to carry out the disclosed technology. Device 700 comprises a processor 750 that controls the overall operation of the computer by executing the measurement device's program instructions which define such operation. The measurement device's program instructions may be stored in a storage device 720 (e.g., magnetic disk, flash disk, database) and loaded into memory 730 when execution of the measurement device's program instructions is desired. Thus, the measurement device's operation will be defined by the measurement device's program instructions stored in memory 730 and/or storage 720, and the measurement device will be controlled by processor 750 executing the measurement device's program instructions. A device 700 also includes one or a plurality of input network interfaces for communicating with other devices via a network (e.g., the internet). A device 700 also includes one or more output network interfaces 710 for communicating with other devices. Device 700 also includes input/output 740 representing devices which allow for user interaction with the computer 700 (e.g., display, keyboard, mouse, speakers, buttons, etc.). One skilled in the art will recognize that an implementation of actual devices will contain other components as well, and that FIG. 12 is a high level representation of some of the components of such a measurement device for illustrative purposes. It should also be understood by one skilled in the art that the method and devices depicted in FIGS. 1 through 11 may be implemented on a device such as is shown in FIG. 12.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A method for determining calculating a change in percent voids between a reference location and a second location in a medium, the method comprising:

(a) using a radar system having a transmitting antenna and a receiving antenna, transmitting and receiving at least one electromagnetic wave to obtain a reference radar measurement for a reference location of a medium, the at least one electromagnetic wave being transmitted at a predetermined incidence angle;

(b) using the predetermined incidence angle, an effective dielectric of the medium, and the reference radar measurement, calculating a transmission angle of the electromagnetic wave through the medium at the reference location and calculating a reference reflection coefficient of an electromagnetic wave reflection at the reference location;

(c) using the radar system transmitting and receiving another electromagnetic wave to obtain a second radar measurement at a second location in the medium, the another electromagnetic wave being transmitted at the predetermined incidence angle;

(d) using the predetermined incidence angle, the effective dielectric of the medium, and the second radar measurement, calculating a transmission angle of the electromagnetic wave through the medium at the second location and calculating a second reflection coefficient of the electromagnetic wave reflection at the second location;

(e) calculating a percent change of reflection coefficients between the reference reflection coefficient and the second reflection coefficient;

(f) graphically generating a % void-percent reflection coefficient (PV-PRC) plot and extracting from the plot a reflection conversion factor correlating changes in reflection coefficient to changes in percent voids in the medium;

(g) using the reflection conversion factor, calculating the change in percent voids between the reference location and the second location based on the determined percent change of reflection coefficients;

(h) repeating steps (c) to (g) for multiple sample locations in an area of the medium, each sample location comprising a said second location; and (i) generating a spatial distribution map of the area of the medium, the spatial distribution map indicating the change in percent voids at the multiple sample locations in the area of the medium.

2. The method of claim 1, wherein calculating the reference reflection coefficient comprises using the radar system to obtain multiple radar measurements over an area, and determining the reference reflection coefficient is based on an average of reflection coefficients for the multiple radar measurements.

3. The method of claim 1, wherein obtaining calculating the reference reflection coefficient comprises determining a dielectric of the medium based on a known Gmm dielectric of the medium and a specified percent voids.

4. The method of claim 1, wherein calculating the reference reflection coefficient and calculating the second reflection coefficients comprise obtaining a ratio of respective reflection amplitudes from an asphalt surface to a reflection amplitude from a conducting surface.

5. The method of claim 4, wherein obtaining a percent change in reflection coefficients from the reference reflection coefficient and the second reflection coefficient comprises calculating the percent change in surface reflection amplitudes between measurements at the reference and second locations.

* * * * *